United States Patent [19]

Seele et al.

[11] Patent Number: 5,162,357

[45] Date of Patent: Nov. 10, 1992

[54] FUNGICIDAL AZOLYLMETHYLOXIRANES

[75] Inventors: Rainer Seele, Fussgoenheim; Norbert Goetz, Worms; Reiner Kober, Fussgoenheim; Bernhard Zipperer, Dirmstein; Eberhard Ammermann, Ludwigshafen; Gisela Lorenz, Neustadt; Joachim Gebhardt, Limburgerhof, all of Fed. Rep. of Germany

[73] Assignee: BASF Aktiengesellschaft, Ludwigshafen, Fed. Rep. of Germany

[21] Appl. No.: 578,400

[22] Filed: Sep. 7, 1990

[30] Foreign Application Priority Data

Sep. 9, 1989 [DE] Fed. Rep. of Germany ....... 3930166
Dec. 21, 1989 [DE] Fed. Rep. of Germany ....... 3942333

[51] Int. Cl.$^5$ ................. A01N 43/653; C07D 249/08
[52] U.S. Cl. .................................... 514/383; 514/184; 548/101; 548/266.2; 548/266.6
[58] Field of Search ................. 548/266.2, 266.6, 101; 514/383, 184

[56] References Cited

FOREIGN PATENT DOCUMENTS 061835 10/1982 European Pat. Off. ......... 548/268.6
94564 11/1983 European Pat. Off. .
196038 10/1986 European Pat. Off. .
330016 8/1989 European Pat. Off. .
330132 8/1989 European Pat. Off. .
332073 9/1989 European Pat. Off. .
334035 9/1989 European Pat. Off. .
352673 1/1990 European Pat. Off. .

*Primary Examiner*—Patricia L. Morris
*Attorney, Agent, or Firm*—Oblon, Spivak, McClelland, Maier & Neustadt

[57] ABSTRACT

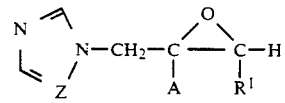

(A, $R^1$) = 5-/6-membered hetaryl, cycloalkyl, tetrahydropyranyl, tetrahydrothiopyranyl, phenyl, biphenyl, naphthyl or benzyl, the substituents A and $R^1$ being unsubstituted or bearing up to three further radicals, with the proviso that at least one of the substituents A and $R^1$ is hetaryl unless $R^1$ is o-methylphenyl; Z=CH, N) and their acid addition salts and metal complexes, with the exception of 2-(imidazol-1-ylmethyl)-2-(4-fluorophenyl)-3-(pyrid-3-yl)-oxirane.

The compounds I are suitable as fungicides.

6 Claims, No Drawings

FUNGICIDAL AZOLYLMETHYLOXIRANES

The present invention relates to novel azolylmethyloxiranes of the formula I

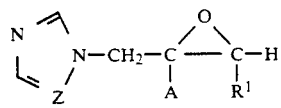

where A and $R^1$ are each 5-membered or 6-membered hetaryl, $C_1-C_8$-alkyl, $C_3-C_8$-cycloalkyl, tetrahydropyranyl, tetrahydrothiopyranyl, phenyl, biphenyl, naphthyl or benzyl, and these substituents may furthermore carry a nitro or amino group or up to three of the following radicals: halogen, $C_1-C_4$-alkyl, partially or completely halogenated $C_1-C_4$-alkyl, $C_1-C_4$-alkoxy or phenoxy, with the proviso that at least one of the substituents A or $R^1$ is one of the hetaryl groups defined above, unless $R^1$ is o-methylphenyl, and Z is CH or N, and their plant-tolerated salts with acids and metal complexes, with the exception of 2-(imidazol-1-ylmethyl)-2-(4-fluorophenyl)-3-(pyrid-3-yl)-oxirane.

The present invention furthermore relates to processes for the preparation of these compounds, their use as fungicides and fungicides which contain these compounds as active substances.

The present invention also relates to oxirane intermediates of the formula III

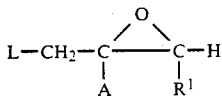

where L is halogen or a radical $R-SO_2-O-$ and R is $C_1-C_6$-alkyl, partially or completely halogenated $C_1-C_4$-alkyl or phenyl which may be substituted by halogen, $C_1-C_4$-alkyl or nitro.

It is known that cis-2-(1,2,4-triazol-1-yl-methyl)-2-(4-chlorophenyl)-3-(4-tert-butylphenyl)-oxirane (European Patent 94,564) and cis-2-(1,2,4-triazol-1-yl-methyl)-2-(4-methylphenyl)-3-(2-fluorophenyl)-oxirane (European Patent 196,038) can be used as fungicides.

Furthermore, EP-A 332 073 mentions azolylmethyloxiranes of the same type as the compounds I, which carry an imidazolylmethyl and a 4-fluorophenyl group in the 2-position and, inter alia, pyridyl in the 3-position.

However, the fungicidal actions of these compounds is satisfactory only to a limited extent, especially at low application rates and concentrations.

It is an object of the present invention to provide novel fungicidal substances.

We have found that this object is achieved by the azolylmethyloxiranes of the formula I which are defined at the outset. We have also found intermediates of the formula III for the preparation of these azolylmethyloxiranes.

The substituents in the novel compounds I and III have the following specific meanings:

A and $R^1$ are each 5-membered or 6-membered hetaryl, in particular pyrrol-2-yl, pyrrol-3-yl, furan-2-yl, thien-2-yl, thien-3-yl, pyrid-2-yl, pyrid-3-yl, pyrid-4-yl, 1,3-diazol-2-yl, oxazol-4-yl, oxazol-5-yl, isoxazol-3-yl, isoxazol-4-yl, isoxazol-5-yl, thiazol-4-yl, thiazol-5-yl, imidazol-4-yl, 1,2,4-triazol-3-yl or 1,3,4-triazol-2-yl, where these substituents may furthermore carry a nitro or amino group or may carry one of the following radicals on each carbon atom: halogen, such as fluorine, chlorine or bromine, $C_1-C_4$-alkyl, such as methyl, ethyl, n-butyl or tert-butyl, $C_1-C_4$-alkyl which is partially or completely halogenated by fluorine, chlorine and/or bromine, such as trifluoromethyl, pentafluoroethyl or 2-chloro-1,1,2-trifluoroethyl, $C_1-C_4$-alkoxy, such as methoxy, ethoxy or tert-butoxy, or phenoxy;

branched or straight-chain $C_1-C_8$-alkyl which may carry nitro, amino or up to three of the radicals stated for the hetaryl group, preferably $C_1-C_6$-alkyl, such as methyl, ethyl, n-propyl, isopropyl, n-butyl, sec-butyl, tert-butyl, n-pentyl or neopentyl;

$C_3-C_8$-cycloalkyl which may carry nitro, amino or up to three of the radicals stated for the hetaryl group, preferably cyclopropyl, cyclobutyl, cyclopentyl or cyclohexyl;

tetrahydropyranyl or tetrahydrothiopyranyl, each of which may carry nitro, amino or up to three of the radicals stated for the hetaryl group, preferably tetrahydropyran4-yl;

phenyl which may carry nitro, amino or up to three of the radicals stated for the hetaryl group, preferably phenyl, 3-nitrophenyl, 4-nitrophenyl, 3-aminophenyl, 4-aminophenyl, halophenyl, such as 2-fluorophenyl, 3-fluorophenyl, 4-fluorophenyl, 2-chlorophenyl, 3-chlorophenyl, 4-chlorophenyl, 2-bromophenyl, 3-bromophenyl or 4-bromophenyl, diahalophenyl, such as 2,3-dichlorophenyl, 2,4-dichlorophenyl, 2,5-dichlorophenyl, 2,6-dichlorophenyl, 2-chloro-4-fluorophenyl, 2-chloro-6-fluorophenyl, $C_1-C_4$-alkylphenyl, such as 4-methylphenyl, 4-ethylphenyl, 4-isopropylphenyl or 4-tert-butylphenyl, halo-$C_1-C_4$-alkylphenyl, such as 2-chloro-6-methylphenyl, $C_1-C_4$-haloalkylphenyl, such as 2-trifluoromethylphenyl, 3-trifluoromethylphenyl or 4-trifluoromethylphenyl, $C_1-C_4$-alkoxyphenyl, such as 2-methoxyphenyl, 3-methoxyphenyl or 4-methoxyphenyl, di-$C_1-C_4$-alkoxyphenyl, such as 2,4-dimethoxyphenyl or 3,4-dimethoxyphenyl, or phenoxyphenyl, such as 3-phenoxyphenyl or 4-phenoxyphenyl;

biphenyl, naphthyl or benzyl, each of which may carry nitro, amino or up to three of the radicals stated for the hetaryl group, preferably 4-biphenyl, 1-naphthyl, 2-naphthyl or benzyl, and L is halogen, such as fluorine, chlorine, bromine or iodine, preferably chlorine or bromine;

a radical $R-SO_2-O-$, where R has the following meanings: branched or straight-chain $C_1-C_6$-alkyl, in particular $C_1-C_4$-alkyl, such as methyl, ethyl, n-butyl or tert-butyl; partially or completely halogenated $C_1-C_4$-alkyl, such as trifluoromethyl, trichloromethyl, pentafluoroethyl or 2-chloro-1,1,2-trifluoroethyl; phenyl which may be substituted by halogen, such as fluorine, chlorine or bromine, $C_1-C_4$-alkyl, such as methyl, ethyl, tert-butyl or nitro.

Particularly preferred compounds I and III are shown in Tables A and B.

The intermediates III are prepared in a very advantageous manner by conventional oxidation of α-haloalkenes of the formula Va or substituted propenals of the formula Vb (cf. G. Dittus in Houben-Weyl-Müller, Methoden der Organischen Chemie, Georg-Thieme-Verlag, Stuttgart, 1965, Vol. VI/3, page 385 et seq.)

and, in the case of the propenals, subsequent reduction and esterification of the formyl group:

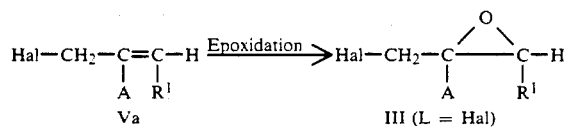
Va            III (L = Hal)

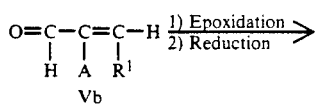
Vb

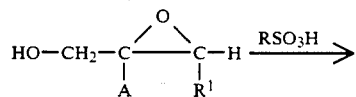

III (L = RSO$_2$—O—)

The oxidation of the olefins Va and Vb is preferably carried out in inert solvents or diluents, such as acetic acid, ethyl acetate, acetone, methyl tert-butyl ether or dimethylformamide, in particular in chlorohydrocarbons, such as methylene chloride, chloroform, carbon tetrachloride or dichloroethane.

If desired, the reaction may be carried out in a buffered medium. Examples of suitable buffers are sodium acetate, sodium carbonate, disodium hydrogen phosphate and benzyltrimethylammonium hydroxide (Triton B).

Peroxycarboxylic acids, such as perbenzoic acid, 3-chloroperbenzoic acid, 4-nitroperbenzoic acid, monoperphthalic acid, peracetic acid, perpropionic acid, permaleic acid, monopersuccinic acid, perpelargonic acid and trifluoroperacetic acid are advantageously used as oxidizing agents.

The oxidation can, if desired, be catalyzed, for example by means of iodine, sodium tungstate or light.

In general, the temperature is from 10° to 100° C., in particular the boiling point of the solvent used.

Alkyl hydroperoxides, such as tert-butyl hydroperoxide, with the use of a catalyst, such as sodium tungstate, pertungstic acid, molybdenum hexacarbonyl or vanadyl acetylacetonate, and alkaline solutions of, for example, 30% strength hydrogen peroxide in methanol, ethanol, acetone or acetonitrile, are also suitable for the oxidation. When one of these stated oxidizing agents is used, some of which can be produced in situ, temperatures of from 20° to 30° C. are preferred.

The oxidizing agent is generally used in equimolar amounts or in a slight excess, for example about 20-50%, based on the olefins Va and Vb.

The reaction is advantageously carried out under atmospheric pressure. Reduced or superatmospheric pressure is possible but generally has no advantages.

After the epoxidation and subsequent reduction, for example with sodium borohydride at about 20° C., the alcohols Vb are converted into their esters by conventional methods (cf. Houben-Müller-Weyl, Methoden der organischen Chemie, Georg-Thieme-Verlag Stuttgart, 1955, Vol. 9, pages 388, 663 and 671). Examples of suitable esters are methanesulfonates, trifluoromethanesulfonates, 2,2,2-trifluoroethanesulfonates, nonafluorobutanesulfonates, benzenesulfonates, 4-methylbenzenesulfonates, 4-bromobenzenesulfonates and 4-nitrobenzenesulfonates.

The propenals Vb can be obtained, for example, by conventional condensation of two aldehydes.

The reaction is advantageously carried out in an inert solvent or diluent at from 10° to 50° C., in particular from 20° to 30° C.

The statements made above are applicable to the pressure.

The olefins Va are obtainable, for example, by conventional chlorination of corresponding propene derivatives CH$_3$CA=CHR$^1$ in the allyl position.

Examples of suitable halogenating reagents are N-chloro- and N-bromosuccinimide in halohydrocarbons, such as carbon tetrachloride, trichloroethane and methylene chloride. The temperature is in general from 20° to 100° C.

The propene derivatives themselves, which are to be halogenated, are obtainable by conventional methods of olefin synthesis (cf. Houben-Weyl-Müller, Methoden der organischen Chemie, Georg-Thieme Verlag Stuttgart, 1972, Vol. V/1b).

The novel intermediates III contain two centers of asymmetry. They are used in the form of racemates, the form in which they are obtained in most preparation processes, but can, if desired, be separated into the pure isomers by the conventional methods, for example chromatography over an optically active adsorbent.

The azolylmethyloxiranes I are obtainable by various methods, preferably by the following methods:

a) Preparation from an azole and an oxirane

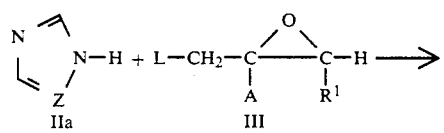
IIa       III

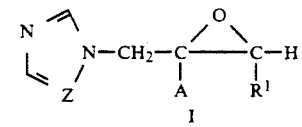
I

The reaction is preferably carried out in a solvent or diluent, particularly preferably with the addition of an organic or inorganic base.

The solvents or diluents used may be ketones, such as acetone, methyl ethyl ketone or cyclohexanone, nitriles, such as acetonitrile or propionitrile, alcohols, such as methanol, ethanol, isopropanol, n-butanol or glycol, esters, such as methyl acetate, ethyl acetate or butyl acetate, ethers, such as tetrahydrofuran, diethyl ether, dimethoxyethane, dioxane or diisopropyl ether, amides, such as dimethylformamide, dimethylacetamide or N-methylpyrrolidone, dimethyl sulfoxide, sulfolane or mixtures of the stated solvents.

Examples of suitable bases are alkali metal hydroxides, such as lithium hydroxide, sodium hydroxide or potassium hydroxide, alkali metal carbonates, such as sodium carbonate or potassium carbonate, bicarbonates, such as sodium bicarbonate or potassium bicarbonate, pyridine and 4-dimethylaminopyridine. However, other conventional bases may also be used.

The reaction takes place particularly advantageously in the presence of a reaction accelerator. For example, metal halides, such as sodium iodide or potassium iodide, quaternary ammonium salts, such as tetrabutylammonium chloride, tetrabutylammonium bromide, tetrabutylammonium iodide, tetrabutylammonium bisulfate or benzyltriethylammonium chloride or bromide, or crown ethers, such as [12]crown-4, [15]crown-5, [18]crown-6, dibenzo[18]crown-6 or dicyclohexano[18]crown-6, are suitable for this purpose.

The starting compounds IIa and III are advantageously used in a stoichiometric ratio, but in some cases an excess of one or other of the components, for example up to 10%, may also be preferable.

The reaction usually takes place at a sufficient rate at above 10° C. In general, the temperature is from 10° to 150° C., in particular from 20° to 120° C., preferably the boiling point of the solvent used.

Since the reaction is not pressure-dependent, atmospheric pressure is advantageously used.

b) Reaction of an Azolyl Anion with an Oxirane

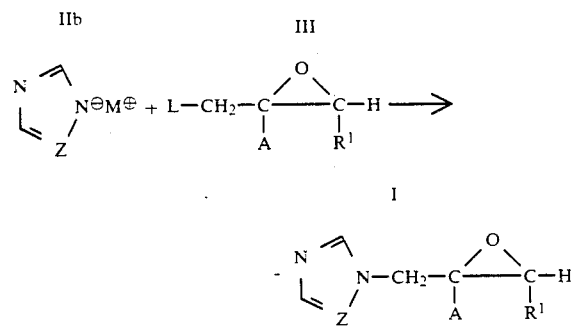

$M^\oplus$ is an alkali metal cation, in particular lithium, sodium or potassium.

As a rule, the reaction is carried out in a solvent or diluent, preferably with the addition of a strong inorganic or organic base.

The solvents or diluents used may be amides, such as dimethylformamide, diethylformamide, dimethylacetamide or diethylacetamide, N-methylpyrrolidone, hexamethylphosphorotriamide or sulfoxides, such as dimethyl sulfoxide or sulfolane.

Examples of suitable bases are alkali metal hydrides, such as lithium hydride, sodium hydride or potassium hydride, alkali metal amides, such as sodium amide or potassium amide, and alkali metal alcoholates, such as sodium tert-butylate or potassium tert-butylate.

As a rule, the reaction takes place at a sufficient rate at above −10° C. In general, the temperature is from −10° to 120° C., in particular from 0° to 100° C., particularly preferably from 20° to 80° C.

Regarding the stoichiometric ratios and the pressure, the statements made for method a) are applicable.

c) Epoxidation of a 3-azolylprop-1-ene

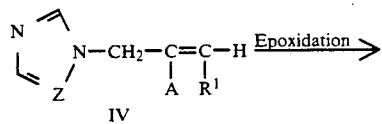

-continued

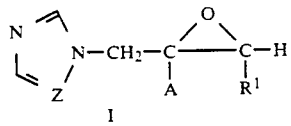

The epoxidation of the olefins IV to give the azolylmethyloxiranes I is carried out by conventional methods (cf. G. Dittus in Houben-Weyl-Müller, Methoden der Organischen Chemie, Georg-Thieme-Verlag Stuttgart, 1965, Vol. VI/3, page 385 et seq.).

The reaction is advantageously carried out in a solvent or diluent, for example in nitriles, such as acetonitrile, sulfoxides, such as dimethyl sulfoxide, formamides, such as dimethylformamide, ketones, such as acetone, ethers, such as diethyl ether or tetrahydrofuran, and in mixtures of the stated solvents. Chlorohydrocarbons, such as methylene chloride and chloroform, are particularly preferred.

In general, the reaction temperature is from 0° to 100° C., preferably from 20° to 80° C. The reaction is particularly preferably carried out at the boiling point of the solvent used.

Regarding the oxidizing agents and the pressure, the statements made in connection with the preparation of the intermediates II are applicable.

The novel compounds I contain two centers of asymmetry. In most preparation processes, they are obtained in the form of racemates, which, if desired, can be separated into the pure isomers by conventional methods, for example by chromatography over an optically active adsorbent. The present invention relates to the racemates as well as the pure isomers, both of which have fungicidal activity.

Suitable addition salts with acids are the salts of acids which do not adversely affect the fungicidal action of I, for example the hydrochlorides, hydrobromides, sulfates, nitrates, phosphates, oxalates and dodecylbenzenesulfonates.

Suitable metal complexes are the complexes of copper, of zinc, of tin, of manganese, of iron, of cobalt or of nickel. The complexes are preferably prepared from the free bases I and salts of the metals with mineral acids, for example the chlorides or sulfates.

PREPARATION EXAMPLES

EXAMPLE 1 cis-2-(1,2,4-Triazol-1-ylmethyl)-2-phenyl-3-(3-pyridyl)-oxirane

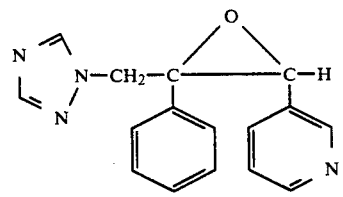

A mixture of 7.8 g (0.11 mol) of 1,2,4-triazole, 150 ml of N,N-dimethylformamide and 26.3 g (0.19 mol) of potassium carbonate was heated for 30 minutes at 50° C. and then cooled to about 20° C., and a solution of 28.2 g (0.09 mol) of cis-2-methylsulfonyloxymethyl-2-phenyl-3-(3-pyridyl)-oxirane in 50 ml of N,N-dimethylformamide was added dropwise. Stirring was carried out for 12 hours at room temperature, after which 100 ml of water were added, the mixture was extracted several times with methyl tertbutyl ether and the organic phase was worked up to give the product. Yield 65%. Mp.: 75° C.

EXAMPLE 2 cis-2-(1,2,4-Triazol-1-ylmethyl)-2-(4-fluorophenyl)-3-(2-methylphenyl)-oxirane

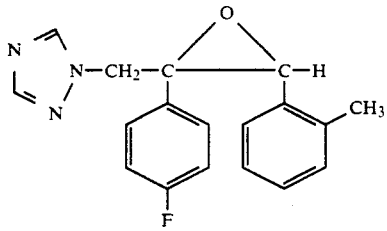

4.9 g (0.07 mol) of 1,2,4-triazole (in 100 ml of N,N-dimethylformamide) were reacted with 20 g (0.06 mol) of cis-2-methylsulfonyloxymethyl-2-(4-fluorophenyl)-3-(2-methylphenyl)-oxirane (in 50 ml of N,N-dimethylformamide) in the presence of 16.4 g (0.12 mol) of potassium carbonate, similarly to Example 1. The crude product was recrystallized from methyl tert-butyl ether/n-hexane. Yield 82%. Mp.: 99°–102° C.

Intermediate α)

2-Phenyl-3-(3-pyridyl)-propenal

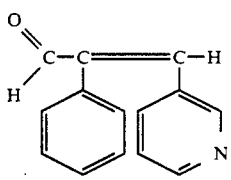

60 g (0.50 mol) of phenylacetaldehyde were rapidly added dropwise to a mixture of 54 g (0.50 mol) of pyridin-3-carbaldehyde in 300 ml of water and 8.4 g (0.21 mol) of sodium hydroxide in 40 ml of water at 10° C. in such a way that the temperature of the solution remained below 30° C. Stirring was carried out for 2 hours at about 20° C., after which 300 ml of water were added, the resulting emulsion was extracted by shaking with methyl tert-butyl ether and the organic phase was worked up to give the product. The crude substance was purified by distillation at 160° C. and 0.6 mbar to give an oil in a yield of 70.5%.

This method was also used to prepare, inter alia, E-2-(4-fluorophenyl)-3-(2-methylphenyl)-propenal by reacting 69 g (0.50 mol) of 4-fluorophenylacetaldehyde with 60 g (0.50 mol) of 2-methylbenzaldehyde in 300 ml of methanol, the crude substance being purified by distillation at 125° C. and 0.1 mbar. Yield 31%.

Intermediate β)

cis-2-Hydroxymethyl-2-phenyl-3-(3-pyridyl)-oxirane

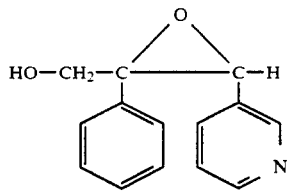

13.5 g of 30% strength hydrogen peroxide solution were slowly added dropwise, at 0° C., to a mixture of 32.2 g (0.152 mol) of 2-phenyl-3-(3-pyridyl)-propenal in 150 150 ml of methanol and 1.7 ml of concentrated sodium hydroxide solution in such a way that the temperature of the mixture remained below 30° C. Stirring was carried out for 6 hours at 20° C., after which 6 g (0.158 mol) of sodium borohydride, dissolved in a little 10% strength sodium hydroxide solution, were added and the mixture was stirred for a further 18 hours. Thereafter, 100 ml of water were added, the resulting emulsion was extracted by shaking with methylene chloride and the organic phase was worked up to give the product. Mp.: 108°–110° C.; yield 82%.

This method was also used to prepare, inter alia, cis-2-hydroxymethyl-2-(4-fluorophenyl)-3-(2-methylphenyl)-oxirane by reacting 37 g (0.154 mol) of E-2-(4-fluorophenyl)-3-(2-methylphenyl)-propenal with 13.5 g of hydrogen peroxide and then reducing the aldehyde group with 5 g (0.132 mol) of sodium borohydride. Yield 61%.

Intermediate α) (=Intermediate of the formula III)

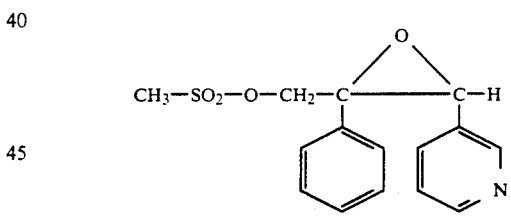

17.2 g (0.15 mol) of methanesulfonyl chloride were stirred into a solution of 28.6 g (0.12 mol) of cis-2-hydroxymethyl-2-phenyl-3-(3-pyridyl)-oxirane in 120 ml of methylene chloride and 26 g of triethylamine at about 20° C. After this mixture had been stirred for 24 hours, it was washed with aqueous sodium bicarbonate solution and water and worked up to give the product. Yield: 69%.

This method was also used to prepare, inter alia, cis-2-(methylsulfonyloxymethyl)-2-(4-fluorophenyl)-3-(2-methylphenyl)-oxirane (compound No. A.117 in Table A) by reacting 13.4 g (0.117 mol) of methanesulfonyl chloride with 24 g (0.093 mol) of cis-2-hydroxymethyl-2-(4-fluorophenyl)-3-(2-methylphenyl)-oxirane in 100 ml of methylene chloride. Yield: 75%.

Table A contains further intermediates III, and Table B further azolylmethyloxiranes I, which can be prepared similarly to the Example compounds.

TABLE 4

$$L-CH_2-C\overset{O}{\underset{A}{\diagdown}}\overset{}{\underset{R^1}{C}}-H \quad (III)$$

| No. | A | $R^1$ | L | mp. [°C.]/$^1$H-NMR [ppm] |
|---|---|---|---|---|
| A.001 | $C_6H_5$ | 3-pyridyl | $OSO_2CH_3$ | 108–110 |
| A.002 | $C_6H_5$ | 2-thienyl | $OSO_2CH_3$ | |
| A.003 | $C_6H_5$ | 2-thienyl | Cl | |
| A.004 | $C_6H_5$ | 2-thienyl | Br | |
| A.005 | $C_6H_5$ | 3-thienyl | $OSO_2CH_3$ | |
| A.006 | $C_6H_5$ | 2-furyl | $OSO_2CH_3$ | |
| A.007 | $C_6H_5$ | 2-pyrryl | $OSO_2CH_3$ | |
| A.008 | $C_6H_5$ | 4-oxazolyl | $OSO_2CH_3$ | |
| A.009 | $C_6H_5$ | 4-thiazolyl | $OSO_2CH_3$ | |
| A.010 | $C_6H_5$ | 5-oxazolyl | $OSO_2CH_3$ | |
| A.011 | $C_6H_5$ | 3-isoxazolyl | $OSO_2CH_3$ | |
| A.012 | $C_6H_5$ | 4-isoxazolyl | $OSO_2CH_3$ | |
| A.013 | $C_6H_5$ | 5-isoxazolyl | $OSO_2CH_3$ | |
| A.014 | $C_6H_5$ | 4-imidazolyl | $OSO_2CH_3$ | |
| A.015 | $C_6H_5$ | 5-thiazolyl | $OSO_2CH_3$ | |
| A.016 | 2-Cl—$C_6H_4$ | 2-thienyl | $OSO_2CH_3$ | |
| A.017 | 4-Cl—$C_6H_4$ | 3-pyridyl | $OSO_2CH_3$ | |
| A.018 | 4-Cl—$C_6H_4$ | 2-thienyl | $OSO_2CH_3$ | |
| A.019 | 4-Cl—$C_6H_4$ | 3-thienyl | $OSO_2CH_3$ | |
| A.020 | 4-Cl—$C_6H_4$ | 2-furyl | $OSO_2CH_3$ | |
| A.021 | 4-Cl—$C_6H_4$ | 4-pyridyl | $OSO_2CH_3$ | |
| A.022 | 2.4-$Cl_2$—$C_6H_3$ | 2-thienyl | $OSO_2CH_3$ | |
| A.023 | 2.4-$Cl_2$—$C_6H_3$ | 2-furyl | $OSO_2CH_3$ | |
| A.024 | 2-F—$C_6H_4$ | 2-thienyl | $OSO_2CH_3$ | |
| A.025 | 2-F—$C_6H_4$ | 3-pyridyl | $OSO_2CH_3$ | |
| A.026 | 4-F—$C_6H_4$ | 2-thienyl | $OSO_2CH_3$ | |
| A.027 | 4-F—$C_6H_4$ | 3-thienyl | $OSO_2CH_3$ | 4.68, 4.39(2d); 4.10(s); 2.84(s) |
| A.028 | 4-F—$C_6H_4$ | 2-furyl | $OSO_2CH_3$ | |
| A.029 | 4-F—$C_6H_4$ | 2-pyridyl | $OSO_2CH_3$ | |
| A.030 | 4-F—$C_6H_4$ | 3-pyridyl | $OSO_2CH_3$ | |
| A.031 | 4-F—$C_6H_4$ | 4-pyridyl | $OSO_2CH_3$ | |
| A.032 | 4-F—$C_6H_4$ | 2-pyrrolyl | $OSO_2CH_3$ | |
| A.033 | 4-F—$C_6H_4$ | 4-oxazolyl | $OSO_2CH_3$ | |
| A.034 | 4-F—$C_6H_4$ | 4-thiazolyl | $OSO_2CH_3$ | |
| A.035 | 4-F—$C_6H_4$ | 5-oxazolyl | $OSO_2CH_3$ | |
| A.036 | 4-F—$C_6H_4$ | 3-isoxazolyl | $OSO_2CH_3$ | |
| A.037 | 4-F—$C_6H_4$ | 4-isoxazolyl | $OSO_2CH_3$ | |
| A.038 | 4-F—$C_6H_4$ | 5-isoxazolyl | $OSO_2CH_3$ | |
| A.039 | 4-F—$C_6H_4$ | 4-imidazolyl | $OSO_2CH_3$ | |
| A.040 | 4-Br—$C_6H_4$ | 2-thienyl | $OSO_2CH_3$ | |
| A.041 | 4-$CF_3$—$C_6H_4$ | 3-thienyl | $OSO_2CH_3$ | |
| A.042 | 4-$CH_3$—$C_6H_4$ | 2-furyl | $OSO_2CH_3$ | |
| A.043 | 4-$OCH_3$—$C_6H_4$ | 2-thienyl | $OSO_2CH_3$ | |
| A.044 | 4-biphenyl | 3-pyridyl | $OSO_2CH_3$ | |
| A.045 | 2-thienyl | $C_6H_5$ | $OSO_2CH_3$ | |
| A.046 | 2-thienyl | 2-Cl—$C_6H_4$ | $OSO_2CH_3$ | |
| A.047 | 2-thienyl | 4-Cl—$C_4H_4$ | $OSO_2CH_3$ | |
| A.048 | 2-thienyl | 2,4-$Cl_2$—$C_6H_3$ | $OSO_2CH_3$ | |
| A.049 | 2-thienyl | 4-F—$C_6H_4$ | $OSO_2CH_3$ | |
| A.050 | 2-thienyl | 2-$CF_3$—$C_6H_4$ | $OSO_2CH_3$ | |
| A.051 | 2-thienyl | 2-$CH_3$—$C_6H_4$ | $OSO_2CH_3$ | |
| A.052 | 2-thienyl | 2-thienyl | $OSO_2CH_3$ | |
| A.053 | 2-thienyl | 3-thienyl | $OSO_2CH_3$ | |
| A.054 | 2-thienyl | 3-pyridyl | $OSO_2CH_3$ | |
| A.055 | 2-thienyl | 2-furyl | $OSO_2CH_3$ | |
| A.056 | 3-thienyl | $C_6H_5$ | $OSO_2CH_3$ | |
| A.057 | 3-thienyl | 2-Cl—$C_6H_4$ | $OSO_2CH_3$ | |
| A.058 | 3-thienyl | 4-Cl—$C_6H_4$ | $OSO_2CH_3$ | |
| A.059 | 3-thienyl | 2,4-$Cl_2$—$C_6H_3$ | $OSO_2CH_3$ | |
| A.060 | 3-thienyl | 4-F—$C_6H_4$ | $OSO_2CH_3$ | |
| A.061 | 3-thienyl | 2-$CF_3$—$C_6H_4$ | $OSO_2CH_3$ | |
| A.062 | 3-thienyl | 2-$CH_3$—$C_6H_4$ | $OSO_2CH_3$ | |
| A.063 | 3-thienyl | 2-thienyl | $OSO_2CH_3$ | |
| A.064 | 3-thienyl | 3-thienyl | $OSO_2CH_3$ | |
| A.065 | 3-thienyl | 3-pyridyl | $OSO_2CH_3$ | |
| A.066 | 3-thienyl | 2-furyl | $OSO_2CH_3$ | |
| A.067 | 2-furyl | $C_6H_5$ | $OSO_2CH_3$ | |
| A.068 | 2-furyl | 2-Cl—$C_6H_4$ | $OSO_2CH_3$ | |
| A.069 | 2-furyl | 4-Cl—$C_6H_4$ | $OSO_2CH_3$ | |
| A.070 | 2-furyl | 4-F—$C_6H_4$ | $OSO_2CH_3$ | |
| A.071 | 2-furyl | 3-pyridyl | $OSO_2CH_3$ | |
| A.072 | 2-furyl | 4-oxazolyl | $OSO_2CH_3$ | |
| A.073 | 3-pyridyl | $C_6H_5$ | $OSO_2CH_3$ | |
| A.074 | 3-pyridyl | 2-Cl—$C_6H_4$ | $OSO_2CH_3$ | |
| A.075 | 3-pyridyl | 4-F—$C_6H_4$ | $OSO_2CH_3$ | |

TABLE 4-continued $$L-CH_2-\underset{A}{\overset{O}{\underset{|}{C}}}\underset{R^1}{\overset{}{\underset{|}{C}}}-H \quad (III)$$

| No. | A | R¹ | L | mp. [°C.]/¹H-NMR [ppm] |
|---|---|---|---|---|
| A.076 | 3-pyridyl | 3-pyridyl | OSO₂CH₃ | |
| A.077 | 4-pyridyl | C₆H₅ | OSO₂CH₃ | |
| A.078 | 4-pyridyl | 2-Cl—C₆H₄ | OSO₂CH₃ | |
| A.079 | 4-pyridyl | 4-Cl—C₆H₄ | OSO₂CH₃ | |
| A.080 | 4-pyridyl | 2-CH₃—C₆H₄ | OSO₂CH₃ | |
| A.081 | 4-pyridyl | 2-CF₃—C₆H₄ | OSO₂CH₃ | |
| A.082 | 4-pyridyl | 2-thienyl | OSO₂CH₃ | |
| A.083 | 4-pyridyl | 3-thienyl | OSO₂CH₃ | |
| A.084 | 4-pyridyl | 2-furyl | OSO₂CH₃ | |
| A.085 | 2-pyridyl | C₆H₅ | OSO₂CH₃ | |
| A.086 | 2-pyridyl | 2-Cl—C₆H₄ | OSO₂CH₃ | |
| A.087 | 2-pyridyl | 2-CH₃—C₆H₄ | OSO₂CH₃ | |
| A.088 | 2-pyridyl | 2-CF₃—C₆H₄ | OSO₂CH₃ | |
| A.089 | 2-pyridyl | 2-thienyl | OSO₂CH₃ | |
| A.090 | 2-pyridyl | 3-thienyl | OSO₂CH₃ | |
| A.091 | 4-oxazolyl | C₆H₅ | OSO₂CH₃ | |
| A.092 | 4-oxazolyl | 2-Cl—C₆H₄ | OSO₂CH₃ | |
| A.093 | 4-thiazolyl | C₆H₅ | OSO₂CH₃ | |
| A.094 | 4-thiazolyl | 2-Cl—C₆H₄ | OSO₂CH₃ | |
| A.095 | 5-oxazolyl | C₆H₅ | OSO₂CH₃ | |
| A.096 | 5-oxazolyl | 2-Cl—C₆H₄ | OSO₂CH₃ | |
| A.097 | 5-thiazolyl | C₆H₅ | OSO₂CH₃ | |
| A.098 | 5-thiazolyl | 2-Cl—C₆H₄ | OSO₂CH₃ | |
| A.099 | 3-isoxazolyl | C₆H₅ | OSO₂CH₃ | |
| A.100 | 3-isoxazolyl | 2-Cl—C₆H₄ | OSO₂CH₃ | |
| A.101 | 4-isoxazolyl | C₆H₅ | OSO₂CH₃ | |
| A.102 | 4-isoxazolyl | 2-Cl—C₆H₄ | OSO₂CH₃ | |
| A.103 | 5-isoxazolyl | C₆H₅ | OSO₂CH₃ | |
| A.104 | 5-isoxazolyl | 2-Cl—C₆H₄ | OSO₂CH₃ | |
| A.105 | 4-imidazolyl | C₆H₅ | OSO₂CH₃ | |
| A.106 | 4-imidazolyl | 2-Cl—C₆H₄ | OSO₂CH₃ | |
| A.107 | cyclohexyl | 2-thienyl | OSO₂CH₃ | |
| A.108 | cyclohexyl | 3-thienyl | OSO₂CH₃ | |
| A.109 | cyclohexyl | 2-furyl | OSO₂CH₃ | |
| A.110 | cyclohexyl | 3-pyridyl | OSO₂CH₃ | |
| A.111 | tert.-C₄H₉ | 2-thienyl | OSO₂CH₃ | |
| A.112 | tert.-C₄H₉ | 3-thienyl | OSO₂CH₃ | |
| A.113 | tert.-C₄H₉ | 2-furyl | OSO₂CH₃ | |
| A.114 | tert.-C₄H₉ | 3-pyridyl | OSO₂CH₃ | |
| A.115 | 4-F—C₆H₄ | 2-CH₃—C₆H₄ | Cl | |
| A.116 | 4-F—C₆H₄ | 2-CH₃—C₆H₄ | Br | |
| A.117 | 4-F—C₆H₄ | 2-CH₃—C₆H₄ | OSO₂CH₃ | 2.20(s), 2.62(s), 4.04(s), 4.18, 4.42(2d) |
| A.118 | 3-F—C₆H₄ | 2-CH₃—C₆H₄ | Cl | |
| A.119 | 3-F—C₆H₄ | 2-CH₃—C₆H₄ | Br | |
| A.120 | 3-F—C₆H₄ | 2-CH₃—C₆H₄ | OSO₂CH₃ | |
| A.121 | 2-F—C₆H₄ | 2-CH₃—C₆H₄ | Cl | |
| A.122 | 2-F—C₆H₄ | 2-CH₃—C₆H₄ | Br | |
| A.123 | 2-F—C₆H₄ | 2-CH₃—C₆H₄ | OSO₂CH₃ | |
| A.124 | 2-Cl—C₆H₄ | 2-CH₃—C₆H₄ | Cl | |
| A.125 | 2-Cl—C₆H₄ | 2-CH₃—C₆H₄ | Br | |
| A.126 | 2-Cl—C₆H₄ | 2-CH₃—C₆H₄ | OSO₂CH₃ | |
| A.127 | 3-Cl—C₆H₄ | 2-CH₃—C₆H₄ | Cl | |
| A.128 | 3-Cl—C₆H₄ | 2-CH₃—C₆H₄ | Br | |
| A.129 | 3-Cl—C₆H₄ | 2-CH₃—C₆H₄ | OSO₂CH₃ | |
| A.130 | 4-Cl—C₆H₄ | 2-CH₃—C₆H₄ | Cl | |
| A.131 | 4-Cl—C₆H₄ | 2-CH₃—C₆H₄ | Br | |
| A.132 | 4-Cl—C₆H₄ | 2-CH₃—C₆H₄ | OSO₂CH₃ | 2.30(s), 2.64(s), 4.06(s), 4.18, 4.44(2d) |
| A.133 | 2,4-Cl₂—C₆H₃ | 2-CH₃—C₆H₄ | Cl | |
| A.134 | 2,4-Cl₂—C₆H₃ | 2-CH₃—C₆H₄ | Br | |
| A.135 | 2,4-Cl₂—C₆H₃ | 2-CH₃—C₆H₄ | OSO₂CH₃ | |
| A.136 | 4-Br—C₆H₄ | 2-CH₃—C₆H₄ | Cl | |
| A.137 | 4-Br—C₆H₄ | 2-CH₃—C₆H₄ | Br | |
| A.138 | 4-Br—C₆H₄ | 2-CH₃—C₆H₄ | OSO₂CH₃ | |
| A.139 | 2-CH₃—C₆H₄ | 2-CH₃—C₆H₄ | Cl | |
| A.140 | 2-CH₃—C₆H₄ | 2-CH₃—C₆H₄ | Br | |
| A.141 | 2-CH₃—C₆H₄ | 2-CH₃—C₆H₄ | OSO₂CH₃ | |
| A.142 | 4-CH₃—C₆H₄ | 2-CH₃—C₆H₄ | Cl | |
| A.143 | 4-CH₃—C₆H₄ | 2-CH₃—C₆H₄ | Br | |
| A.144 | 4-CH₃—C₆H₄ | 2-CH₃—C₆H₄ | OSO₂CH₃ | |
| A.145 | 2-CF₃—C₆H₄ | 2-CH₃—C₆H₄ | Cl | |
| A.146 | 2-CF₃—C₆H₄ | 2-CH₃—C₆H₄ | Br | |
| A.147 | 2-CF₃—C₆H₄ | 2-CH₃—C₆H₄ | OSO₂CH₃ | |
| A.148 | 3-CF₃—C₆H₄ | 2-CH₃—C₆H₄ | Cl | |

TABLE 4-continued $$L-CH_2-\underset{A}{\underset{|}{C}}\overset{O}{\underset{}{\diagup}}\underset{R^1}{\underset{|}{C}}-H \quad \text{(III)}$$

| No. | A | R¹ | L | mp. [°C.]/¹H-NMR [ppm] |
|---|---|---|---|---|
| A.149 | 3-CF₃—C₆H₄ | 2-CH₃—C₆H₄ | Br | |
| A.150 | 3-CF₃—C₆H₄ | 2-CH₃—C₆H₄ | OSO₂CH₃ | |
| A.151 | 4-CF₃—C₆H₄ | 2-CH₃—C₆H₄ | Cl | |
| A.152 | 4-CF₃—C₆H₄ | 2-CH₃—C₆H₄ | Br | |
| A.153 | 4-CF₃—C₆H₄ | 2-CH₃—C₆H₄ | OSO₂CH₃ | |
| A.154 | 4-OCH₃—C₆H₄ | 2-CH₃—C₆H₄ | Cl | |
| A.155 | 4-OCH₃—C₆H₄ | 2-CH₃—C₆H₄ | Br | |
| A.156 | 4-OCH₃—C₆H₄ | 2-CH₃—C₆H₄ | OSO₂CH₃ | |
| A.157 | C₆H₅ | 2-CH₃—C₆H₄ | Cl | |
| A.158 | C₆H₅ | 2-CH₃—C₆H₄ | Br | |
| A.159 | C₆H₅ | 2-CH₃—C₆H₄ | OSO₂CH₃ | 2.30(s), 2.62(s), 4.04(s), 4.16, 4.42(2d) |
| A.160 | 1-naphthyl | 2-CH₃—C₆H₄ | Cl | |
| A.161 | 1-naphthyl | 2-CH₃—C₆H₄ | Br | |
| A.162 | 1-naphthyl | 2-CH₃—C₆H₄ | OSO₂CH₃ | |
| A.163 | CH₃ | 2-CH₃—C₆H₄ | Cl | |
| A.164 | CH₃ | 2-CH₃—C₆H₄ | Br | |
| A.165 | CH₃ | 2-CH₃—C₆H₄ | OSO₂CH₃ | 1.64(s), 2.24(s), 2.68(s), 3.82, 3.94(2d), 4.20(s) |
| A.166 | tert.-C₄H₉ | 2-CH₃—C₆H₄ | Cl | |
| A.167 | tert.-C₄H₉ | 2-CH₃—C₆H₄ | Br | |
| A.168 | tert.-C₄H₉ | 2-CH₃—C₆H₄ | OSO₂CH₃ | |
| A.169 | cyclohexyl | 2-CH₃—C₆H₄ | Cl | |
| A.170 | cyclohexyl | 2-CH₃—C₆H₄ | Br | |
| A.171 | cyclohexyl | 2-CH₃—C₆H₄ | OSO₂CH₃ | |
| A.172 | 4-tetrahydropyranyl | 2-CH₃—C₆H₄ | Cl | |
| A.173 | 4-tetrahydropyranyl | 2-CH₃—C₆H₄ | Br | |
| A.174 | 4-tetrahydropyranyl | 2-CH₃—C₆H₄ | OSO₂CH₃ | |

TABLE B $$\underset{Z}{\overset{N\diagdown}{\underset{\diagup}{\nwarrow}}}N-CH_2-\underset{A}{\underset{|}{C}}\overset{O}{\underset{}{\diagup}}\underset{R^1}{\underset{|}{C}}-H \quad \text{(I)}$$

| No. | A | R¹ | Z | mp. [°C.]/IR [cm⁻¹] |
|---|---|---|---|---|
| B.001 | phenyl | 3-pyridyl | N | 75 |
| B.002 | phenyl | 2-pyridyl | N | |
| B.003 | phenyl | 4-pyridyl | N | |
| B.004 | phenyl | 2-thienyl | N | |
| B.005 | phenyl | 2-thienyl | CH | |
| B.006 | phenyl | 3-thienyl | N | |
| B.007 | phenyl | 3-thienyl | CH | |
| B.008 | phenyl | 2-furyl | N | |
| B.009 | phenyl | 2-furyl | CH | |
| B.010 | phenyl | 2-pyrryl | N | |
| B.011 | phenyl | 3-pyrryl | N | |
| B.012 | phenyl | 4-oxazolyl | N | |
| B.013 | phenyl | 4-thiazolyl | N | |
| B.014 | phenyl | 5-oxazolyl | N | |
| B.015 | phenyl | 3-isoxazolyl | N | |
| B.016 | phenyl | 4-isoxazolyl | N | |
| B.017 | phenyl | 5-isoxazolyl | N | |
| B.018 | phenyl | 4-imidazolyl | N | |
| B.019 | phenyl | 4-imidazolyl | CH | |
| B.020 | phenyl | 5-thiazolyl | N | |
| B.021 | 2-Cl—C₆H₄ | 2-pyridyl | N | |
| B.022 | 2-Cl—C₆H₄ | 2-thienyl | N | |
| B.023 | 2-Cl—C₆H₄ | 3-thienyl | N | |
| B.024 | 2-Cl—C₆H₄ | 2-furyl | N | |
| B.025 | 2-Cl—C₆H₄ | 2-pyrryl | N | |
| B.026 | 2-Cl—C₆H₄ | 3-thiazolyl | N | |
| B.027 | 2-Cl—C₆H₄ | 4-isoxazolyl | N | |
| B.028 | 4-Cl—C₆H₄ | 2-pyridyl | N | |
| B.029 | 4-Cl—C₆H₄ | 3-pyridyl | N | |
| B.030 | 4-Cl—C₆H₄ | 4-pyridyl | N | |
| B.031 | 4-Cl—C₆H₄ | 2-thienyl | N | |
| B.032 | 4-Cl—C₆H₄ | 3-thienyl | N | |
| B.033 | 4-Cl—C₆H₄ | 2-furyl | N | |
| B.034 | 4-Cl—C₆H₄ | 2-pyrrolyl | N | |
| B.035 | 4-Cl—C₆H₄ | 4-oxazolyl | N | |

TABLE B-continued (I)

$$\underset{Z}{\overset{N}{\underset{\diagup}{\bigg\langle}}}N-CH_2-\underset{A}{\overset{\diagup O \diagdown}{C\text{———}C}}-H \atop R^1$$

| No. | A | R¹ | Z | mp. [°C.]/IR [cm⁻¹] |
|---|---|---|---|---|
| B.036 | 4-Cl—C₆H₄ | 5-oxazolyl | N | |
| B.037 | 4-Cl—C₆H₄ | 4-thiazolyl | N | |
| B.038 | 4-Cl—C₆H₄ | 4-imidazolyl | N | |
| B.039 | 2,4-Cl₂—C₆H₃ | 2-pyridyl | N | |
| B.040 | 2,4-Cl₂—C₆H₃ | 3-pyridyl | N | |
| B.041 | 2,4-Cl₂—C₆H₃ | 2-thienyl | N | |
| B.042 | 2,4-Cl₂—C₆H₃ | 3-thienyl | N | |
| B.043 | 2,4-Cl₂—C₆H₃ | 2-furyl | N | |
| B.044 | 2,4-Cl₂—C₆H₃ | 2-pyrrolyl | N | |
| B.045 | 2,4-Cl₂—C₆H₃ | 4-thiazolyl | N | |
| B.046 | 2,4-Cl₂—C₆H₃ | 4-isoxazolyl | N | |
| B.047 | 2-F—C₆H₄ | 3-pyridyl | N | |
| B.048 | 2-F—C₆H₄ | 2-thienyl | N | |
| B.049 | 2-F—C₆H₄ | 3-thienyl | N | |
| B.050 | 2-F—C₆H₄ | 2-furyl | N | |
| B.051 | 2-F—C₆H₄ | 2-pyrrolyl | N | |
| B.052 | 4-F—C₆H₄ | 2-pyridyl | N | |
| B.053 | 4-F—C₆H₄ | 3-pyridyl | N | |
| B.054 | 4-F—C₆H₄ | 4-pyridyl | N | |
| B.055 | 4-F—C₆H₄ | 2-thienyl | N | |
| B.056 | 4-F—C₆H₄ | 2-thienyl | CH | |
| B.057 | 4-F—C₆H₄ | 3-thienyl | N | 78–80 |
| B.058 | 4-F—C₆H₄ | 3-thienyl | CH | 1607, 1513, 1226, 841 |
| B.059 | 4-F—C₆H₄ | 2-furyl | N | |
| B.060 | 4-F—C₆H₄ | 2-furyl | CH | |
| B.061 | 4-F—C₆H₄ | 4-pyrrolyl | N | |
| B.062 | 4-F—C₆H₄ | 3-pyrrolyl | N | |
| B.063 | 4-F—C₆H₄ | 4-oxazolyl | N | |
| B.064 | 4-F—C₆H₄ | 4-oxazolyl | CH | |
| B.065 | 4-F—C₆H₄ | 5-oxazolyl | N | |
| B.066 | 4-F—C₆H₄ | 5-oxazolyl | CH | |
| B.067 | 4-F—C₆H₄ | 4-thiazolyl | N | |
| B.068 | 4-F—C₆H₄ | 4-thiazolyl | CH | |
| B.069 | 4-F—C₆H₄ | 5-thiazolyl | N | |
| B.070 | 4-F—C₆H₄ | 5-thiazolyl | CH | |
| B.071 | 4-F—C₆H₄ | 3-isoxazolyl | N | |
| B.072 | 4-F—C₆H₄ | 4-isoxazolyl | N | |
| B.073 | 4-F—C₆H₄ | 5-isoxazolyl | N | |
| B.074 | 4-F—C₆H₄ | 4-imidazolyl | N | |
| B.075 | 4-Br—C₆H₄ | 3-pyridyl | N | |
| B.076 | 4-Br—C₆H₄ | 2-thienyl | N | |
| B.077 | 4-Br—C₆H₄ | 3-thienyl | N | |
| B.078 | 4-Br—C₆H₄ | 2-furyl | N | |
| B.079 | 4-Br—C₆H₄ | 4-isoxazolyl | N | |
| B.080 | 4-CF₃—C₆H₄ | 3-pyridyl | N | |
| B.081 | 4-CF₃—C₆H₄ | 2-thienyl | N | |
| B.082 | 4-CF₃—C₆H₄ | 3-thienyl | N | |
| B.083 | 4-CF₃—C₆H₄ | 2-furyl | N | |
| B.084 | 4-CF₃—C₆H₄ | 4-isoxazolyl | N | |
| B.085 | 4-CH₃—C₆H₄ | 3-pyridyl | N | |
| B.086 | 4-CH₃—C₆H₄ | 2-thienyl | N | |
| B.087 | 4-CH₃—C₆H₄ | 3-thienyl | N | |
| B.088 | 4-CH₃—C₆H₄ | 2-furyl | N | |
| B.089 | 4-CH₃—C₆H₄ | 3-isoxazolyl | N | |
| B.090 | 4-CH₃—C₆H₄ | 4-thiazolyl | N | |
| B.091 | 4-OCH₃—C₆H₄ | 3-pyridyl | N | |
| B.092 | 4-OCH₃—C₆H₄ | 2-thienyl | N | |
| B.093 | 4-OCH₃—C₆H₄ | 3-thienyl | N | |
| B.094 | 4-OCH₃—C₆H₄ | 4-oxazolyl | N | |
| B.095 | 4-OCH₃—C₆H₄ | 2-furyl | N | |
| B.096 | 4-biphenyl | 3-pyridyl | N | |
| B.097 | 4-biphenyl | 2-thienyl | N | |
| B.098 | 2-thienyl | C₆H₅ | N | |
| B.099 | 2-thienyl | C₆H₅ | CH | |
| B.100 | 2-thienyl | 2-Cl—C₆H₄ | N | 119–121 |
| B.101 | 2-thienyl | 2-Cl—C₆H₄ | N × CuSO₄ | |
| B.102 | 2-thienyl | 2-Cl—C₆H₄ | CH | |
| B.103 | 2-thienyl | 4-Cl—C₆H₄ | N | |
| B.104 | 2-thienyl | 4-Cl—C₆H₄ | CH | |
| B.105 | 2-thienyl | 2,4-Cl₂—C₆H₃ | N | |
| B.106 | 2-thienyl | 2,4-Cl₂—C₆H₃ | CH | |
| B.107 | 2-thienyl | 2-Br—C₆H₄ | N | |
| B.108 | 2-thienyl | 2-F—C₆H₄ | N | |
| B.109 | 2-thienyl | 4-F—C₆H₄ | N | |
| B.110 | 2-thienyl | 4-Br—C₆H₄ | N | |

TABLE B-continued

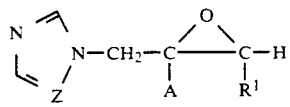
(I)

| No. | A | R¹ | Z | mp. [°C.]/IR [cm⁻¹] |
|---|---|---|---|---|
| B.111 | 2-thienyl | 2-CH$_3$—C$_6$H$_4$ | N | |
| B.112 | 2-thienyl | 2-CH$_3$—C$_6$H$_4$ | CH | |
| B.113 | 2-thienyl | 4-CH$_3$—C$_6$H$_4$ | N | |
| B.114 | 2-thienyl | 2,4-(CH$_3$)$_2$—C$_6$H$_3$ | N | |
| B.115 | 2-thienyl | 2-CF$_3$—C$_6$H$_4$ | N | |
| B.116 | 2-thienyl | 2-CF$_3$—C$_6$H$_4$ | CH | |
| B.117 | 2-thienyl | 4-CF$_3$—C$_6$H$_4$ | N | |
| B.118 | 2-thienyl | 2-OCH$_3$—C$_6$H$_4$ | N | |
| B.119 | 2-thienyl | 4-NO—C$_6$H$_4$ | N | |
| B.120 | 2-thienyl | 2-naphthyl | N | |
| B.121 | 2-thienyl | 2-thienyl | N | |
| B.122 | 2-thienyl | 3-thienyl | N | |
| B.123 | 2-thienyl | 3-pyridyl | N | |
| B.124 | 2-thienyl | 2-furyl | N | |
| B.125 | 2-thienyl | 4-isoxazolyl | N | |
| B.126 | 2-thienyl | CH$_3$ | N | |
| B.127 | 3-thienyl | C$_6$H$_5$ | N | |
| B.128 | 3-thienyl | C$_6$H$_5$ | CH | |
| B.129 | 3-thienyl | 2-Cl—C$_6$H$_4$ | N | |
| B.130 | 3-thienyl | 2-Cl—C$_6$H$_4$ | CH | |
| B.131 | 3-thienyl | 4-Cl—C$_6$H$_4$ | N | |
| B.132 | 3-thienyl | 2,4-Cl$_2$—C$_6$H$_3$ | N | |
| B.133 | 3-thienyl | 2-Br—C$_6$H$_4$ | N | |
| B.134 | 3-thienyl | 4-Br—C$_6$H$_4$ | N | |
| B.135 | 3-thienyl | 2-F—C$_6$H$_4$ | N | |
| B.136 | 3-thienyl | 4-F—C$_6$H$_4$ | N | |
| B.137 | 3-thienyl | 2-CH$_3$—C$_6$H$_4$ | N | |
| B.138 | 3-thienyl | 2-CH$_3$—C$_6$H$_4$ | CH | |
| B.139 | 3-thienyl | 2,4-(CH$_3$)$_2$—C$_6$H$_3$ | N | |
| B.140 | 3-thienyl | 2-CF$_3$—C$_6$H$_4$ | N | |
| B.141 | 3-thienyl | 2-CF$_3$—C$_6$H$_4$ | CH | |
| B.142 | 3-thienyl | 4-CF$_3$—C$_6$H$_4$ | N | |
| B.143 | 3-thienyl | 2-OCH$_3$—C$_6$H$_4$ | N | |
| B.144 | 3-thienyl | 4-NO$_2$—C$_6$H$_4$ | N | |
| B.145 | 3-thienyl | 2-naphthyl | N | |
| B.146 | 3-thienyl | 2-thienyl | N | |
| B.147 | 3-thienyl | 3-thienyl | N | |
| B.148 | 3-thienyl | 3-pyridyl | N | |
| B.149 | 3-thienyl | 2-furyl | N | |
| B.150 | 3-thienyl | 4-oxazolyl | N | |
| B.151 | 3-thienyl | 4-thiazolyl | N | |
| B.152 | 3-thienyl | tert.-C$_4$H$_9$ | N | |
| B.153 | 2-furyl | C$_6$H$_5$ | N | |
| B.154 | 2-furyl | C$_6$H$_5$ | CH | |
| B.155 | 2-furyl | 2-Cl—C$_6$H$_4$ | N | |
| B.156 | 2-furyl | 2-Cl—C$_6$H$_4$ | CH | |
| B.157 | 2-furyl | 4-Cl—C$_6$H$_4$ | N | |
| B.158 | 2-furyl | 2,4-Cl$_2$—C$_6$H$_3$ | N | |
| B.159 | 2-furyl | 2-Br—C$_6$H$_4$ | N | |
| B.160 | 2-furyl | 4-Br—C$_6$H$_4$ | N | |
| B.161 | 2-furyl | 2-F—C$_6$H$_4$ | N | |
| B.162 | 2-furyl | 4-F—C$_6$H$_4$ | N | |
| B.163 | 2-furyl | 2-CH$_3$—C$_6$H$_4$ | N | |
| B.164 | 2-furyl | 2-CH$_3$—C$_6$H$_4$ | CH | |
| B.165 | 2-furyl | 2-CF$_3$—C$_6$H$_4$ | N | |
| B.166 | 2-furyl | 2-CF$_3$—C$_6$H$_4$ | CH | |
| B.167 | 2-furyl | 4-CF$_3$—C$_6$H$_4$ | N | |
| B.168 | 2-furyl | 2-OCH$_3$—C$_6$H$_4$ | N | |
| B.169 | 2-furyl | 4-biphenyl | N | |
| B.170 | 2-furyl | 2-thienyl | N | |
| B.171 | 2-furyl | 3-thienyl | N | |
| B.172 | 2-furyl | 2-furyl | N | |
| B.173 | 2-furyl | 4-oxazolyl | N | |
| B.174 | 2-furyl | 3-pyridyl | N | |
| B.175 | 2-furyl | 4-thiazolyl | N | |
| B.176 | 3-pyridyl | C$_6$H$_5$ | N | |
| B.177 | 3-pyridyl | 2-Cl—C$_6$H$_4$ | N | |
| B.178 | 3-pyridyl | 4-Cl—C$_6$H$_4$ | N | |
| B.179 | 3-pyridyl | 2,4-Cl$_2$—C$_6$H$_3$ | N | |
| B.180 | 3-pyridyl | 2-F—C$_6$H$_4$ | N | |
| B.181 | 3-pyridyl | 4-F—C$_6$H$_4$ | N | |
| B.182 | 3-pyridyl | 2-CF$_3$—C$_6$H$_4$ | N | |
| B.183 | 3-pyridyl | 2-CH$_3$—C$_6$H$_4$ | N | |
| B.184 | 3-pyridyl | 2-Br—C$_6$H$_4$ | N | |
| B.185 | 4-pyridyl | C$_6$H$_5$ | N | |

TABLE B-continued $$\text{(I)}$$

Structure: N-heterocycle(Z)-N-CH₂-C(A)(-O-)C-H(R¹) (epoxide)

| No. | A | R¹ | Z | mp. [°C.]/IR [cm⁻¹] |
|---|---|---|---|---|
| B.186 | 4-pyridyl | 2-Cl—C₆H₄ | N | |
| B.187 | 4-pyridyl | 4-Cl—C₆H₄ | N | |
| B.188 | 4-pyridyl | 2,4-Cl₂—C₆H₃ | N | |
| B.189 | 4-pyridyl | 2-F—C₆H₄ | N | |
| B.190 | 4-pyridyl | 4-F—C₆H₄ | N | |
| B.191 | 4-pyridyl | 2-CF₃—C₆H₄ | N | |
| B.192 | 4-pyridyl | 2-CH₃—C₆H₄ | N | |
| B.193 | 4-pyridyl | 2-Br—C₆H₄ | N | |
| B.194 | 4-pyridyl | 2-thienyl | N | |
| B.195 | 4-pyridyl | 3-thienyl | N | |
| B.196 | 4-pyridyl | 2-furyl | N | |
| B.197 | 4-pyridyl | 3-pyridyl | N | |
| B.198 | 2-pyridyl | C₆H₅ | N | |
| B.199 | 2-pyridyl | 2-Cl—C₆H₄ | N | |
| B.200 | 2-pyridyl | 4-Cl—C₆H₄ | N | |
| B.201 | 2-pyridyl | 2,4-Cl₂—C₆H₃ | N | |
| B.202 | 2-pyridyl | 4-F—C₆H₄ | N | |
| B.203 | 2-pyridyl | 2-CF₃—C₆H₄ | N | |
| B.204 | 2-pyridyl | 2-CH₃—C₆H₄ | N | |
| B.205 | 4-oxazolyl | C₆H₅ | N | |
| B.206 | 4-oxazolyl | 2-Cl—C₆H₄ | N | |
| B.207 | 4-oxazolyl | 2-CF₃—C₆H₄ | N | |
| B.208 | 4-oxazolyl | 2-CH₃—C₆H₄ | N | |
| B.209 | 4-thiazolyl | C₆H₅ | N | |
| B.210 | 4-thiazolyl | 2-Cl—C₆H₄— | N | |
| B.211 | 4-thiazolyl | 2-CF₃—C₆H₄ | N | |
| B.212 | 4-thiazolyl | 2-CH₃—C₆H₄ | N | |
| B.213 | 4-thiazolyl | 2-thienyl | N | |
| B.214 | 4-thiazolyl | 2-furyl | N | |
| B.215 | 4-thiazolyl | 3-pyridyl | N | |
| B.216 | 5-oxazolyl | C₆H₅ | N | |
| B.217 | 5-oxazolyl | 2-Cl—C₆H₄ | N | |
| B.218 | 5-oxazolyl | 2-CH₃—C₆H₄ | N | |
| B.219 | 5-oxazolyl | 3-thienyl | N | |
| B.220 | 5-thiazolyl | C₆H₅ | N | |
| B.221 | 5-thiazolyl | 2-Cl—C₆H₄ | N | |
| B.222 | 5-thiazolyl | 2-CH₃—C₆H₄ | N | |
| B.223 | 5-thiazolyl | 2-furyl | N | |
| B.224 | 3-isoxazolyl | C₆H₅ | N | |
| B.225 | 3-isoxazolyl | 2-Cl—C₆H₄ | N | |
| B.226 | 3-isoxazolyl | 2-CH₃—C₆H₄ | N | |
| B.227 | 3-isoxazolyl | 3-thienyl | N | |
| B.228 | 4-isoxazolyl | C₆H₅ | N | |
| B.229 | 4-isoxazolyl | 2-Cl—C₆H₄ | N | |
| B.230 | 5-isoxazolyl | C₆H₅ | N | |
| B.231 | 5-isoxazolyl | 2-Cl—C₆H₄ | N | |
| B.232 | 4-imidazolyl | C₆H₅ | N | |
| B.233 | 4-imidazolyl | 2-Cl—C₆H₄ | N | |
| B.234 | cyclohexyl | 2-thienyl | N | |
| B.235 | cyclohexyl | 3-thienyl | N | |
| B.236 | cyclohexyl | 2-furyl | N | |
| B.237 | cyclohexyl | 2-pyridyl | N | |
| B.238 | cyclohexyl | 3-pyridyl | N | |
| B.239 | cyclohexyl | 4-pyridyl | N | |
| B.240 | cyclohexyl | 4-thiazolyl | N | |
| B.241 | cyclohexyl | 5-oxazolyl | N | |
| B.242 | tert.-C₄H₉ | 2-thienyl | N | |
| B.243 | tert.-C₄H₉ | 3-thienyl | N | |
| B.244 | tert.-C₄H₉ | 2-furyl | N | |
| B.245 | tert.-C₄H₉ | 2-pyridyl | N | |
| B.246 | tert.-C₄H₉ | 3-pyridyl | N | |
| B.247 | tert.-C₄H₉ | 4-pyridyl | N | |
| B.248 | tert.-C₄H₉ | 4-isoxazolyl | N | |
| B.249 | 4-F—C₆H₄ | 2-CH₃—C₆H₄ | N | 99–102 |
| B.250 | 4-F—C₆H₄ | 2-CH₃—C₆H₄ | CH | 1606, 1512, 1225, 1193, 845, 748 |
| B.251 | 3-F—C₆H₄ | 2-CH₃—C₆H₄ | N | |
| B.252 | 3-F—C₆H₄ | 2-CH₃—C₆H₄ | CH | |
| B.253 | 2-F—C₆H₄ | 2-CH₃—C₆H₄ | N | |
| B.254 | 2-F—C₆H₄ | 2-CH₃—C₆H₄ | CH | |
| B.255 | 2,4-F₂—C₆H₃ | 2-CH₃—C₆H₄ | N | |
| B.256 | 2,4-F₂—C₆H₃ | 2-CH₃—C₆H₄ | CH | |
| B.257 | 2-Cl—C₆H₄ | 2-CH₃—C₆H₄ | N | |
| B.258 | 2-Cl—C₆H₄ | 2-CH₃—C₆H₄ | CH | |
| B.259 | 3-Cl—C₆H₄ | 2-CH₃—C₆H₄ | N | |
| B.260 | 3-Cl—C₆H₄ | 2-CH₃—C₆H₄ | CH | |

TABLE B-continued $$\text{N} \diagup\!\!\diagdown\!\!\text{N}-\text{CH}_2-\underset{A}{\text{C}}\underset{}{\diagup\!\!\overset{O}{\diagdown}}\underset{R^1}{\text{C}}-\text{H} \quad (I)$$

| No. | A | R¹ | Z | mp. [°C.]/IR [cm⁻¹] |
|---|---|---|---|---|
| B.261 | 4-Cl—C₆H₄ | 2-CH₃—C₆H₄ | N | 105–108 |
| B.262 | 4-Cl—C₆H₄ | 2-CH₃—C₆H₄ | CH | 99–102 |
| B.263 | 2,3-Cl₂—C₆H₃ | 2-CH₃—C₆H₄ | N | |
| B.264 | 2,3-Cl₂—C₆H₃ | 2-CH₃—C₆H₄ | CH | |
| B.265 | 2,4-Cl₂—C₆H₃ | 2-CH₃—C₆H₄ | N | |
| B.266 | 2,4-Cl₂—C₆H₃ | 2-CH₃—C₆H₄ | CH | |
| B.267 | 2-Br—C₆H₄ | 2-CH₃—C₆H₄ | N | |
| B.268 | 2-Br—C₆H₄ | 2-CH₃—C₆H₄ | CH | |
| B.269 | 4-Br—C₆H₄ | 2-CH₃—C₆H₄ | N | |
| B.270 | 4-Br—C₆H₄ | 2-CH₃—C₆H₄ | CH | |
| B.271 | 2-Cl-4-F—C₆H₃ | 2-CH₃—C₆H₄ | N | |
| B.272 | 2-Cl-4-F—C₆H₃ | 2-CH₃—C₆H₄ | CH | |
| B.273 | 3-NO₂—C₆H₄ | 2-CH₃—C₆H₄ | N | |
| B.274 | 3-NO₂—C₆H₄ | 2-CH₃—C₆H₄ | CH | |
| B.275 | 4-NO₂—C₆H₄ | 2-CH₃—C₆H₄ | N | |
| B.276 | 4-NO₂—C₆H₄ | 2-CH₃—C₆H₄ | CH | |
| B.277 | 3-NH₂—C₆H₄ | 2-CH₃—C₆H₄ | N | |
| B.278 | 3-NH₂—C₆H₄ | 2-CH₃—C₆H₄ | CH | |
| B.279 | 2-CH₃—C₆H₄ | 2-CH₃—C₆H₄ | N | |
| B.280 | 2-CH₃—C₆H₄ | 2-CH₃—C₆H₄ | CH | |
| B.281 | 4-CH₃—C₆H₄ | 2-CH₃—C₆H₄ | N | |
| B.282 | 4-CH₃—C₆H₄ | 2-CH₃—C₆H₄ | CH | |
| B.283 | 2-CF₃—C₆H₄ | 2-CH₃—C₆H₄ | N | |
| B.284 | 2-CF₃—C₆H₄ | 2-CH₃—C₆H₄ | CH | |
| B.285 | 3-CF₃—C₆H₄ | 2-CH₃—C₆H₄ | N | |
| B.286 | 3-CF₃—C₆H₄ | 2-CH₃—C₆H₄ | CH | |
| B.287 | 4-CF₃—C₆H₄ | 2-CH₃—C₆H₄ | N | |
| B.288 | 4-CF₃—C₆H₄ | 2-CH₃—C₆H₄ | CH | |
| B.289 | 4-tert.-C₄H₉—C₆H₄ | 2-CH₃—C₆H₄ | N | |
| B.290 | 4-tert.-C₄H₉—C₆H₄ | 2-CH₃—C₆H₄ | CH | |
| B.291 | 2-OCH₃—C₆H₄ | 2-CH₃—C₆H₄ | N | |
| B.292 | 2-OCH₃—C₆H₄ | 2-CH₃—C₆H₄ | CH | |
| B.293 | 3-OCH₃—C₆H₄ | 2-CH₃—C₆H₄ | N | |
| B.294 | 3-OCH₃—C₆H₄ | 2-CH₃—C₆H₄ | CH | |
| B.295 | 3-OCH₃—C₆H₄ | 2-CH₃—C₆H₄ | N | |
| B.296 | 4-OCH₃—C₆H₄ | 2-CH₃—C₆H₄ | CH | |
| B.297 | 4-C₄H₉O—C₆H₄ | 2-CH₃—C₆H₄ | N | |
| B.298 | 4-C₄H₉O—C₆H₄ | 2-CH₃—C₆H₄ | CH | |
| B.299 | C₆H₅ | 2-CH₃—C₆H₄ | N | 1492, 1447, 1271, 1139, 758, 698 |
| B.300 | C₆H₅ | 2-CH₃—C₆H₄ | CH | |
| B.301 | 4-C₆H₅—C₆H₄ | 2-CH₃—C₆H₄ | N | |
| B.302 | 4-C₆H₅—C₆H₄ | 2-CH₃—C₆H₄ | CH | |
| B.303 | 1-naphthyl | 2-CH₃—C₆H₄ | N | |
| B.304 | 1-naphthyl | 2-CH₃—C₆H₄ | CH | |
| B.305 | 2-naphthyl | 2-CH₃—C₆H₄ | N | |
| B.306 | 2-naphthyl | 2-CH₃—C₆H₄ | CH | |
| B.307 | 4-C₆H₅—O—C₆H₄ | 2-CH₃—C₆H₄ | N | |
| B.308 | 4-C₆H₅—O—C₆H₄ | 2-CH₃—C₆H₄ | CH | |
| B.309 | CH₃ | 2-CH₃—C₆H₄ | N | |
| B.310 | CH₃ | 2-CH₃—C₆H₄ | CH | |
| B.311 | C₂H₅ | 2-CH₃—C₆H₄ | N | |
| B.312 | C₂H₅ | 2-CH₃—C₆H₄ | CH | |
| B.313 | tert.-C₄H₉ | 2-CH₃—C₆H₄ | N | |
| B.314 | tert.-C₄H₉ | 2-CH₃—C₆H₄ | CH | |
| B.315 | cyclopropyl | 2-CH₃—C₆H₄ | N | |
| B.316 | cyclopropyl | 2-CH₃—C₆H₄ | CH | |
| B.317 | cyclopentyl | 2-CH₃—C₆H₄ | N | |
| B.318 | cyclopentyl | 2-CH₃—C₆H₄ | CH | |
| B.319 | cyclohexyl | 2-CH₃—C₆H₄ | N | |
| B.320 | cyclohexyl | 2-CH₃—C₆H₄ | CH | |
| B.321 | tetrahydropyran-4-yl | 2-CH₃—C₆H₄ | N | |
| B.32 | tetrahydropyran-4-yl | 2-CH₃—C₆H₄ | CH | |

The azolylmethyloxiranes I have an excellent action on a broad spectrum of phytopathogenic fungi, in par- The fungicidal compounds are of particular interest for controlling a large number of fungi in various crops or their seeds, especially wheat, rye, barley, oats, rice, indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
*Puccinia* species in cereals,
*Rhizoctonia solani* in cotton,
*Ustilago* species in cereals and sugar cane,
*Venturia inaequalis* (scab) in applies,
*Helminthosporium* species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
*Fusarium* and *Verticillium* species in various plants,
*Plasmopara viticola* in grapes,
*Alternaria* species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., against Paecilomyces variotii.

When the active ingredients are used for treating seed, amounts of from 0.001 to 50, and preferably from 0.01 to 10, g per kg of seed are generally sufficient.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. A solution of 90 parts by weight of compound no. B.001 is mixed with 10 parts by weight of N-methyl-α-pyrrolidone, which is suitable for application in the form of very fine drops.

II. A mixture of 20 parts by weight of compound no. B.100, 80 parts by weight of xylene, 10 parts by weight of the adduct of 8 to 10 moles of ethylene oxide and 1 mole of oleic acid-N-monoethanolamide, 5 parts by weight of the calcuim salt of dodecylbenzenesulfonic acid, and 5 parts by weight of the adduct of 40 moles of ethylene oxide and 1 mole of castor oil. By finely dispersing the mixture in 100,000 parts by weight of water, an aqueous dispersion is obtained.

III. An aqueous dispersion of 20 parts by weight of compound no. B.001, 40 parts by weight of cyclohexanone, 30 parts by weight of isobutanol, 20 parts by weight of the adduct of 40 moles of ethylene oxide and 1 mole of castor oil.

IV. An aqueous dispersion of 20 parts by weight of compound no. B.100, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil.

V. A hammer-milled mixture of 80 parts by weight of compound no. B.301, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. B.302 and 97 parts by weight of particulate kaolin. The dust contains 3 wt % of the active ingredient.

VII. An intimate mixture of 30 parts by weight of compound no. B.313, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. B.314, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. B.301, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

USE EXAMPLES

For comparison purposes, cis-2-(1,2,4-triazol-1-ylmethyl)-2-(4-methylphenyl)-3-(2-fluorophenyl)-oxirane (V1), disclosed in EP 196,038, and cis-2-(1,2,4-triazol-1-ylmethyl)-2-(4-chlorophenyl)-3-(4-tert-butylphenyl)-oxirane (V2), disclosed in EP 94,564, were used:

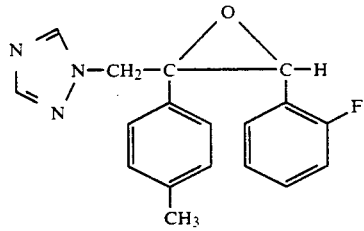

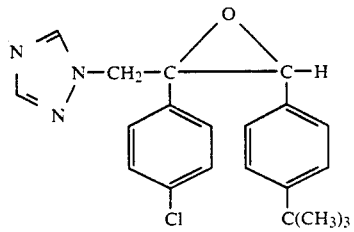

EXAMPLE 1

Action on Wheat Brown Rust

Leaves of pot-grown wheat seedlings of the "Kanzler" variety were dusted with spores of brown rust (Puccinia recondita). The pots were then placed for 24 hours at 20° to 22° C. in a high-humidity (90-95%) chamber. During this period the spores germinated and the germ tubes penetrated the leaf tissue. The infected plants were then sprayed to runoff with 0.006 wt % aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients B.249 and B.261, applied as 0.006 wt % spray liquors, have a better fungicidal action (100%) than prior art comparative agents V1 (80%) and V2 (50%).

EXAMPLE 2

Action on Wheat Mildew

Leaves of pot-grown wheat seedlings of the "Kanzler" variety were sprayed with 0.006 wt % aqueous liquors containing (dry basis) 80% of active ingredient and 20% of emulsifier, and dusted, 24 hours after the sprayed-on layer had dried, with spores of wheat mildew (Erysiphe graminis var. tritici). The plants were then set up in the greenhouse at from 20° to 22° C. and a relative humidity of from 75 to 80%. The extent of mildew spread was assessed after 7 days.

The results show that active ingredients B.249 and B.261, applied as 0.006 wt % spray liquors, had a better fungicidal action (100%) than prior art comparative compounds V1 (80%) and V2 (65%).

EXAMPLE 3

Action on *Pyrenophora teres*

Barley seedlings of the "Igri" variety were sprayed to runoff at the 2-leaf stage with 0.05 wt % aqueous suspensions containing (dry basis) 80% of active ingredient and 20% emulsifier. After 24 hours the plants were inoculated with a spore suspension of the fungus Pyrenophora teres and placed for 48 hours in a high-humidity climatic cabinet kept at 18° C. The plants were then cultivated for a further 5 days in the greenhouse at 20°-22° C. and relative humidity of 70%. The extent of fungus spread was then determined.

The results show that active ingredients B.249, B.250, B.261 and B.262, applied as 0.05 wt % spray liquors, had a better fungicidal action (100%) than prior art comparative agent V1 (65%).

We claim:

1. A compound of the formula I

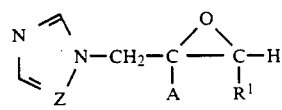

where the substituents have the following meanings:
A, $R^1$: $C_1$-$C_8$-alkyl, $C_3$-$C_8$-cycloalkyl, tetrahydropyranyl,
tetrahydrothiopyranyl, phenyl, biphenyl, naphthyl or benzyl,
and these substituents may furthermore bear a nitro or amino group or up to three of the following radicals:
halogen, $C_1$-$C_4$-alkyl, partially or completely halogenated $C_1$-$C_4$-alkyl, $C_1$-$C_4$-alkoxy or phenoxy; or hetaryl, with the proviso that at least one of the substituents A or $R^1$ is hetaryl;
Z: N;
and wherein hetaryl is selected from the group consisting of substituted or unsubstituted pyrrol-2-yl, pyrrol-3-yl, furan-2-yl, thien-2-yl, and thien-3-yl, wherein the substituents are selected from a nitro group, an amino group and one or more of the following substituents attached to ring carbon atoms: halo, $C_1$-$C_4$-alkyl, halogenated $C_1$-$C_4$-alkyl, or $C_1$-$C_4$-alkoxy groups;
or a plant-tolerated acid addition salt or metal complex thereof.

2. A fungicidal composition containing a fungicidally effective amount of a compound of the formula I

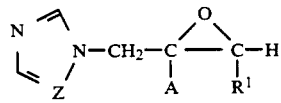

where the substituents have the following meanings:
A, $R^1$: $C_1$-$C_8$-alkyl, $C_3$-$C_8$-cycloalkyl, tetrahydropyranyl,
tetrahydrothiopyranyl, phenyl, biphenyl, naphthyl or benzyl,
and these substituents may furthermore bear a nitro or amino group or up to three of the following radicals:
halogen, $C_1$-$C_4$-alkyl, partially or completely halogenated $C_1$-$C_4$-alkyl, $C_1$-$C_4$-alkoxy or phenoxy;

or hetaryl with the proviso that at least one of the substituents A or $R^1$ is hetaryl;

Z: N;

and wherein hetaryl is selected from the group consisting of substituted or unsubstituted pyrrol-2-yl, pyrrol-3-yl, furan-2-yl, thien-2-yl, and thien-3-yl, wherein the substituents are selected from a nitro group, an amino group and one or more of the following substituents attached to ring carbon atoms: halo, $C_1$–$C_4$-alkyl, halogenated $C_1$–$C_4$-alkyl, or $C_1$–$C_4$-alkoxy groups;

or a plant-tolerated acid addition salt or metal complex as set forth in claim 1, and an inert solid or liquid carrier.

3. A process for combating fungi, wherein a fungicidally effective amount of a compound of the formula

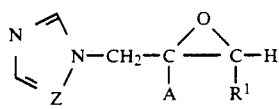   I where the substituents have the following meanings:

A, $R^1$: $C_1$–$C_8$-alkyl, $C_3$–$C_8$-cycloalkyl, tetrahydropyranyl, tetrahydrothiopyranyl, phenyl, biphenyl, naphthyl or benzyl, and these substituents may furthermore bear a nitro or amino group or up to three of the following radicals:

halogen, $C_1$–$C_4$-alkyl, partially or completely halogenated $C_1$–$C_4$-alkyl, $C_1$–$C_4$-alkoxy or phenoxy; or hetaryl with the proviso that at least one of the substituents A or $R^1$ is hetaryl;

Z: N;

and wherein hetaryl is selected from the group consisting of substituted or unsubstituted pyrrol-2-yl, pyrrol-3-yl, furan-2-yl, thien-2-yl, and thien-3-yl, wherein the substituents are selected from a nitro group, an amino group and one or more of the following substituents attached to ring carbon atoms: halo, $C_1$–$C_4$-alkyl, halogenated $C_1$–$C_4$-alkyl, or $C_1$–$C_4$-alkoxy groups;

or a plant-tolerated acid addition salt or metal complex thereof is applied to the fungi, the plants threatened by fungus attack, the plant habitat, or the seed of threatened plants.

4. A compound according to claim 1, wherein at least one of A and $R^1$ is 2- or 3-thienyl or 2- or 3-thienyl substituted by a member selected from the group consisting of one nitro group; one amino group; and one to three groups selected from the group consisting of halogen, $C_1$–$C_4$-alkyl, $C_1$–$C_4$-haloalkyl, $C_1$–$C_4$-alkoxy and phenoxy.

5. A compound according to claim 4 wherein at least one of A and $R^1$ is 2-thienyl or 3-thienyl.

6. A compound according to claim 5 wherein A is 4-fluorophenyl and $R^1$ is 3-thienyl.

* * * * *